United States Patent
Thieme et al.

[11] Patent Number: 5,871,905
[45] Date of Patent: Feb. 16, 1999

[54] REDUCTION OF FALSE POSITIVES IN ORAL-FLUID BASED IMMUNOASSAYS

[75] Inventors: Thomas Thieme, Independence; Nanette Klimkow, Beaverton, both of Oreg.

[73] Assignee: Epitope, Inc., Beaverton, Oreg.

[21] Appl. No.: 707,446

[22] Filed: Sep. 4, 1996

[51] Int. Cl.$^6$ .................... C12Q 1/70; C12Q 1/68; G01N 33/53; A61B 5/00
[52] U.S. Cl. .................... 435/5; 435/6; 435/71; 435/72; 128/760; 128/771
[58] Field of Search ............ 435/5, 6, 7; 128/760, 128/771

[56] References Cited

U.S. PATENT DOCUMENTS

| | | | |
|---|---|---|---|
| D. 348,735 | 7/1994 | Grootbuizen | D24/225 |
| 4,256,724 | 3/1981 | Rutner et al. | 424/1 |
| 4,256,725 | 3/1981 | Rutner et al. | 424/1 |
| 4,454,232 | 6/1984 | Breglio et al. | 436/506 |
| 4,956,274 | 9/1990 | Khanna et al. | 435/7 |
| 4,956,302 | 9/1990 | Gordon et al. | 436/161 |
| 4,959,303 | 9/1990 | Milburn et al. | 435/7 |
| 4,960,691 | 10/1990 | Gordon et al. | 435/6 |
| 4,981,786 | 1/1991 | Dafforn et al. | 435/7 |
| 5,120,643 | 6/1992 | Ching et al. | 435/790 |
| 5,136,026 | 8/1992 | Römisch et al. | 530/416 |
| 5,339,829 | 8/1994 | Thieme et al. | 128/760 |

FOREIGN PATENT DOCUMENTS

| | | | |
|---|---|---|---|
| 0 689 052 | 12/1995 | European Pat. Off. | G01N 33/96 |
| WO 94/22011 | 9/1994 | WIPO | G01N 33/543 |

*Primary Examiner*—Lynette F. Smith
*Assistant Examiner*—Brett Nelson
*Attorney, Agent, or Firm*—Townsend and Townsend and Crew LLP

[57] ABSTRACT

This invention relates to the use and composition of materials which, when added to oral fluid samples, make such samples suitable for use with microparticle-based immunoassays. In one embodiment, this invention provides a method of reducing false positives in assays for the detection of an analyte in an oral fluid sample. The method involves providing an oral fluid sample combined with a bile acid or salt where the bile acid or salt is present in a concentration sufficient to reduce the rate of occurrence of false positives in said oral fluid based immunoassays.

18 Claims, 5 Drawing Sheets

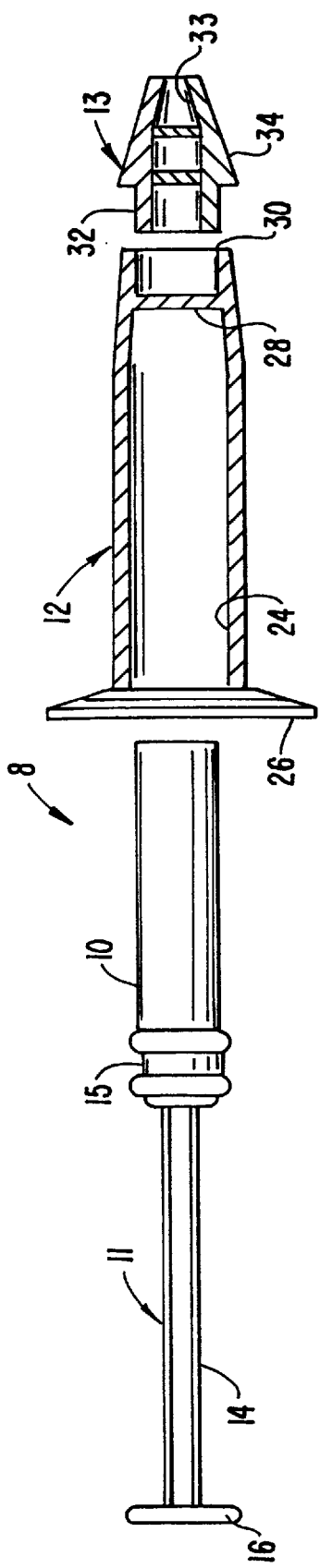
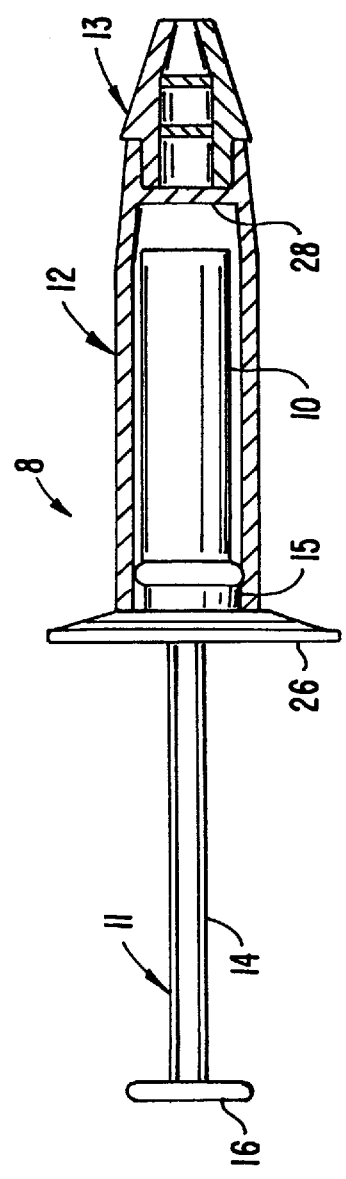
FIG. 1A.
FIG. 1B.

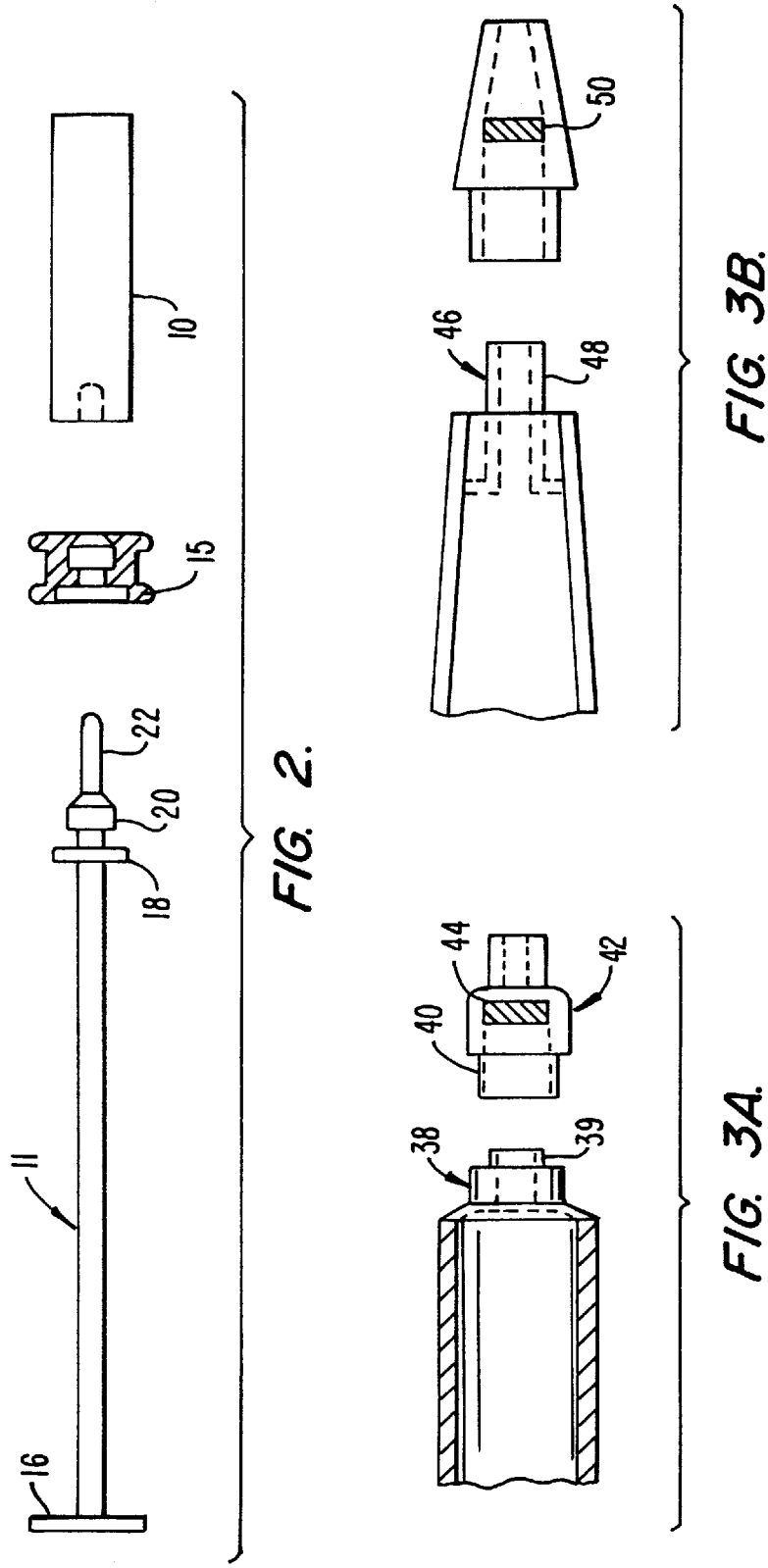

REDUCTION OF FALSE POSITIVES IN ORAL-FLUID BASED IMMUNOASSAYS

FIELD OF THE INVENTION

This invention pertains to the field of immunoassays. More particularly, this invention relates to the use and composition of materials which, when added to oral fluid samples, make such samples suitable for use with microparticle-based immunoassays.

BACKGROUND OF THE INVENTION

Immunoassays utilizing colored microparticles are widely used to provide simple, sensitive field and laboratory tests for analytes of clinical interest such as drugs, antibodies, and antigens. Such tests have been applied to analytes in urine, serum, and whole blood.

In typical immunoassays that use a particulate moiety as a detectable label, colored microparticles such as gelatin, dyed latex, or colloidal gold are labeled with a material (e.g. antibody) which binds the analyte of interest. The most common assay utilizing microparticle indicators is the lateral flow immunochromatography assay (see, e.g., U.S. Pat. No. 5,120,643, British Patent GB 2204398A, and European patent EP 0323605 B1). In most lateral flow immunochromatography assays, microparticles are dried onto a sample application pad (typically glass fiber) which in turn is affixed to one end of a strip of chromatographic medium such as nitrocellulose. Another material binding to the analyte of interest is affixed to the chromatographic medium at or near the end opposite to the end having the application pad.

The liquid sample to be analyzed is placed on the pad, causing the suspension of the microparticles into the liquid and allowing any analyte in the liquid sample to bind to the analyte-binding material attached to the microparticles. The liquid sample leaves the application pad by diffusion and capillary action and begins to migrate along the nitrocellulose strip carrying the microparticles down the strip along with the liquid. When the liquid containing the suspended microparticles arrives at the region of the chromatographic strip bearing the second binding material, the analyte (if present in the original sample) will form a molecular bridge between the analyte-binding material on the microparticles and the analyte-binding material affixed to the strip, resulting in the immobilization of the microparticles at that point on the strip where the analyte-binding material is affixed. This immobilization of the microparticles results in a visible signal (e.g., a colored band or dot) at this point on the strip. If the analyte is not present in the sample, the microparticles will continue past this location on the chromatographic strip and a visible signal will not be produced.

A significant problem in the implementation of microparticle-based immunochromatography assays is prevention of non-specific binding of the microparticles to each other (agglutination), to the sample application pad, and to the nitrocellulose strip. Such non-specific binding (binding that is not mediated by specific recognition of the analyte and analyte-binding materials) results in false-positive test results.

A number of strategies have been used to prevent this non-specific binding. These strategies include "blocking" of the sample application pad and nitrocellulose strip with materials such as casein, gelatin, serum albumin, polyethylene glycol, polyvinyl alcohol, and a number of ionic and non-ionic detergents. In other approaches the microparticles are dried on the sample application pad in the presence of some of these same "blocking" materials and "chromatographic transport facilitating agents".

Although the relevant literature typically states that samples suitable for microparticle-based immunoassays include "physiological fluids, for example blood, saliva, ocular lens fluid, cerebral spinal fluid, sweat, urine, milk, ascites fluid, mucous, synovial fluid, peritoneal fluid amniotic fluid or the like" (see, e.g., Devereaux et al. EP 0 323 605 B1), in practice such assays have only been applied to blood and urine samples. Saliva, and other oral fluid samples, in particular, pose significant problems in these assays because of the low level of some analytes of clinical interest (e.g. antibodies and antigens relevant to infectious disease), and because of the presence of mucopolysaccharides in saliva which amplify and change the character of the nonspecific binding problems of the microparticles. Accordingly, the routine use of the blocking agents cited above has not proven adequate to produce a practical microparticle-based immunoassay which utilizes a sample containing an oral fluid.

SUMMARY OF THE INVENTION

This invention relates to the use and composition of materials which, when added to saliva or other oral fluid samples, make such samples suitable for use with microparticle-based immunochromatography assays. In particular, such materials consist of various mixtures of bile salts (or their corresponding acid forms) and, optionally, agents which chelate or sequester divalent ions. It was a discovery of this invention that the addition of a bile salt or acid to an oral fluid sample, before or during an immunoassay utilizing a particulate detectable label, significantly decreases the incidence of false positives generated in the assay of that oral fluid sample.

Thus, in one embodiment, this invention provides a method of reducing false positives in assays, more preferably in immunoassays, for the detection of an analyte in an oral fluid sample. The method involves the step of providing an oral fluid sample combined with a bile acid or salt. The bile acid or salt is present in a concentration sufficient to reduce the rate of occurrence of false positives in immunoassays characterized by the use of a particulate moiety as a detectable label. Preferred immunoassays include any of the immunoassays disclosed herein with immunoassays utilizing gelatin, colloidal gold, glass, or plastic microspheres as detectable labels being most preferred.

In a particularly preferred embodiment, suitable bile acids or salts include deoxycholic acid (deoxycholate salt), cholic acid (cholate salt), chenodeoxycholic acid (chenodeoxycholate salt), glycodeoxycholic acid (glycodeoxycholate salt), or taurodeoxycholic acid (taurodeoxycholate salt), with deoxycholic acid (deoxycholate salt) being most preferred. In another embodiment, the bile salts or acids do not include ursodeoxycholate (ursodeoxycholic acid).

In another embodiment, the method can further involve contacting a chelator of divalent cations, or a material that otherwise binds and/or sequesters divalent cations, with the oral fluid sample. Preferred chelators include, but are not limited to EDTA, EGTA, NTA, CDTA, sodium citrate, and a chelating resin, with EDTA being most preferred. EDTA concentrations in the final sample used in the assay range from about 0.005M to about 0.05M.

The oral fluid samples can be obtained according to any of the methods disclosed herein with preferred collection means including, but not limited to a sponge, an absorbent pad, a salt-impregnated absorbent pad, an aspirator, and a mouth rinse. Particularly preferred oral fluid samples have a significantly higher mucosal transudate content than saliva.

The methods of this invention can be practiced with assays for virtually any analyte. The analytes may include, but are not limited to antibodies to HIV, antibodies to HTLV, antibodies to *Helicobacter pylori,* antibodies to hepatitis, antibodies to measles, antibodies to mumps, antibodies to rubella, cotinine, cocaine, benzoylecgonine, benzodizazpine, tetrahydrocannabinol, nicotine, ethanol theophylline, phenytoin, acetaminophen, lithium, diazepam, nortryptyline, secobarbital, phenobarbitol, theophylline, testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, IGA and sex hormone binding globulin; and other analytes including glucose, cholesterol, caffeine, cholesterol, corticosteroid binding globulin, PSA, or DHEA binding glycoprotein with the methods being particularly well suited to the detection of HIV antibodies.

In one particularly preferred embodiment, the method involves providing an oral fluid sample combined with a bile salt or acid (e.g., deoxycholate) where the oral fluid sample is contacted with a chelator (or sequestration matrix or binder) of divalent cations before, during, or after combination of the oral fluid with the bile salt or acid. The sample is then assayed, most preferably in a lateral flow chromatography immunoassay.

In another embodiment, this invention provides a kit for the detection of an analyte in an oral fluid sample. The kit includes, but is not limited to a means for collecting an oral fluid sample; a reagent comprising a bile salt or acid; and a means for performing an immunoassay utilizing a particulate moiety as a detectable label. The bile salt and/or acid can include one or more of the bile salts or acids described herein. The kit can optionally include a chelator of divalent cations such as EDTA, EGTA, NTA, CDTA, sodium citrate, or a chelating resin.

The means for collecting an oral fluid sample includes, but is not limited to, any of means disclosed herein including a sponge, an absorbent pad, a salt-impregnated absorbent pad, an aspirator, or a mouth rinse. One particularly preferred means for collecting an oral fluid sample includes an absorbent sponge or pad and a device for extracting the oral fluid sample from the absorbent sponge or pad. The device for extracting said oral fluid sample from the absorbent pad or sponge can further comprise a means for combining a reagent comprising a bile salt or acid with the oral fluid sample. The device for extracting the oral fluid sample from the absorbent pad or sponge can be a syringe or syringe-like means and includes means such as those discussed in U.S. Pat. Nos. 5,339,829, and 5,479,937.

In one particularly preferred embodiment, the device for extracting the oral fluid sample from the absorbent pad or sponge comprises a syringe plunger attached to the absorbent pad or sponge and a syringe barrel wherein said syringe barrel comprises a passageway containing a reagent comprising a bile salt or acid which then combines with the oral fluid sample when the oral fluid sample is expelled from the syringe. The reagent in this embodiment can further include a chelator of divalent cations. The means for performing an immunoassay in this embodiment is preferably a lateral flow immunoassay, more preferably a lateral flow immunoassay that detects antibodies to agents of infectious disease, most preferably an immunoassay that detects antibodies to HIV or HIV antigens.

Definitions

As used herein, the term "analyte" is used to refer to a moiety that is to be detected in a particular assay. Analytes can be atoms (elements), molecules, or groups of molecules. Analytes commonly detected in the assays of this invention include, but are not limited to antibodies, antigens, growth factors, enzymes, therapeutic drugs, drugs of abuse, and the like. Particularly preferred analytes include antibodies and antigens relevant to infectious and non-infections disease.

As used herein, an "immunoassay" is an assay that utilizes an antibody or antigen to specifically bind to the analyte. The immunoassay is characterized by the use of specific binding to a particular antibody as opposed to other physical or chemical properties to isolate, target, and quantify the analyte.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology,* W. E. Paul, ed., Raven Press, N.Y. (1993) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

The phrase "specifically binds to an analyte" or "specifically immunoreactive with", when referring to an antibody refers to a binding reaction which is determinative of the presence of the analyte in the presence of a heterogeneous population of molecules such as proteins and other biologics (i.e., such as may be found in oral fluid). Thus, under designated immunoassay conditions, the specified antibodies bind to a particular analyte and do not bind in a significant amount to other analytes present in the sample. A variety of immunoassay formats may be used to select antibodies specifically immunoreactive with a particular analyte. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

A "label" is a composition detectable by spectroscopic, photochemical, biochemical, immunochemical, electrical, optical or chemical means.

A "chelator", "chelating resin", "binder", "sequestration agent", or "sequester of divalant cations" refers to a composition that binds divalent cations. The binding can be reversible or irreversible. Binding of the divalent cations generally renders them substantially unable to participate in chemical reactions with other moieties with which they come in contact. Chelators are well known to those of skill in the art and include ethylenediamine tetraacetate (EDTA), sodium citrate, ethyleneglycol-bis(β-aminoethylether-N,N, N',N'-tetraacetic acid (EGTA), trans-1,2-diaminocyclohexane-N,N,N',N'-tetraacetic acid (CDTA), nitriloacetic acid (NTA), resins that contain moieties that bind divalent cations and the like. Chelators that remain in solid phase in the solution in question are referred to as chelating resins. Chelating resins can be used to pull the subject ion (e.g., $Ca^{2+}$) out of solution. Chelating reins are well known to those of skill in the art and include, but are not limited to chelex resins containing iminodiacetate ions, or resins containing free base polyamines, or aminophosphonic acid, and the like.

As used herein, a "functionally equivalent analogue" is an analogue of a bile salt or acid that, when combined with an oral fluid sample, significantly reduces the incidence of false positives in an immunoassay that utilizes a particulate label (e.g., in a lateral flow immunochromatography assay) as compared to the same oral fluid sample lacking the bile salt or acid when tested in the same assay.

The term "false positive" is used to refer to a positive assay result indicating the presence of a particular analyte in a sample when that analyte is not really present in the sample. A "false negative" refers to the opposite result; a negative assay result indicating the absence of particular analyte in a sample when that analyte is actually present in the sample.

HIV is a family of viruses, e.g., HIV-1 and HIV-2, well known to those of skill in the art. The original isolates of these viruses were variably referred to as lymphadenopathy virus (LAV, Barre-Sinoussi et al. (1983) *Science* 220:868–871), human T-cell lymphotropic virus-III (HTLV-III, Popovic et al. (1984) *Science* 224:497) and AIDS-associated retrovirus (ARV, Levy et al. (1984) *Science* 225 840–842). These isolates were originally termed "human T-cell lymphotropic retrovirus (hTLR)". Subsequently, the name HIV has been given to these retroviruses by an international committee. Thus, HIV (and particularly HIV-1) shall be used herein as an equivalent to hTLR. Examples of HIV-1 were previously called LAV, ARV and HTLV-III. Among the identifying characteristics of HIV retroviruses are (i) being an etiologic of AIDS, (ii) being cytopathic in vitro, (iii) having a tropism for CD4-bearing cells, and (iv) having elements trans-activating the expression of viral genes acting at the LTR level.

The term "HIV-1 protein" is used herein to refer to a protein (p), glycoprotein (gp), or fragment thereof that is characteristically found in, and therefore characteristic of HIV-1. Typical HIV-1 proteins include, but are not limited to gp160, gp120, p65, p55, p51, gp41, p31, p24 and p18 (number refers to apparent molecular weight in kilodaltons).

The term "preservative", as used herein, is intended to designate a substance showing antimicrobial properties, in particular bactericidal properties and preferably also antifungal properties.

The term "OraSure sample or specimen" refers to an oral fluid sample collected using the ORASURE® oral fluid collection device produced by Epitope Inc., Beaverton, Oreg., USA. Oral fluid samples obtained using the ORASURE® device typically show an increased concentration of mucosal transudate and a higher antibody concentration as compared to saliva.

The terms "syringe" or "syringe-like" device, when used with reference to a device for extracting an oral fluid sample from a sponge or absorbent pad generally refer to a cylinder or barrel with a slidable piston or plunger. The sponge or absorbent pad is placed inside the cylinder or barrel where the piston or plunger compresses compresses the pad or sponge thereby releasing the oral fluid sample which then passes through a fluid passageway at the outlet end of the barrel. The syringe or syringe-like device can also comprise one or more reagent(s) (e.g., a bile salt or acid) contained in the passageway, effective to be released into the oral fluid when such is expelled from the barrel. The passageway may be defined by a cartridge that is detachably mounted on the barrel and which may contain the reagent(s). Suitable syringe or syringe-like devices are described in U.S. Pat. Nos. 5,339,829, and 5,479,937.

BRIEF DESCRIPTION OF THE DRAWINGS

FIGS. 1A and 1B are cross-sectional side views of an oral fluid collection device according to an embodiment of the present invention, shown before (FIG. 1A) and after (FIG. 1B) plunger engagement with a barrel in the device.

FIG. 2 is an assembly view of the plunger and pad in the FIG. 1 device.

FIGS. 3A and 3B show alternative cartridge and syringe barrel embodiments.

DETAILED DESCRIPTION

Figure 4:
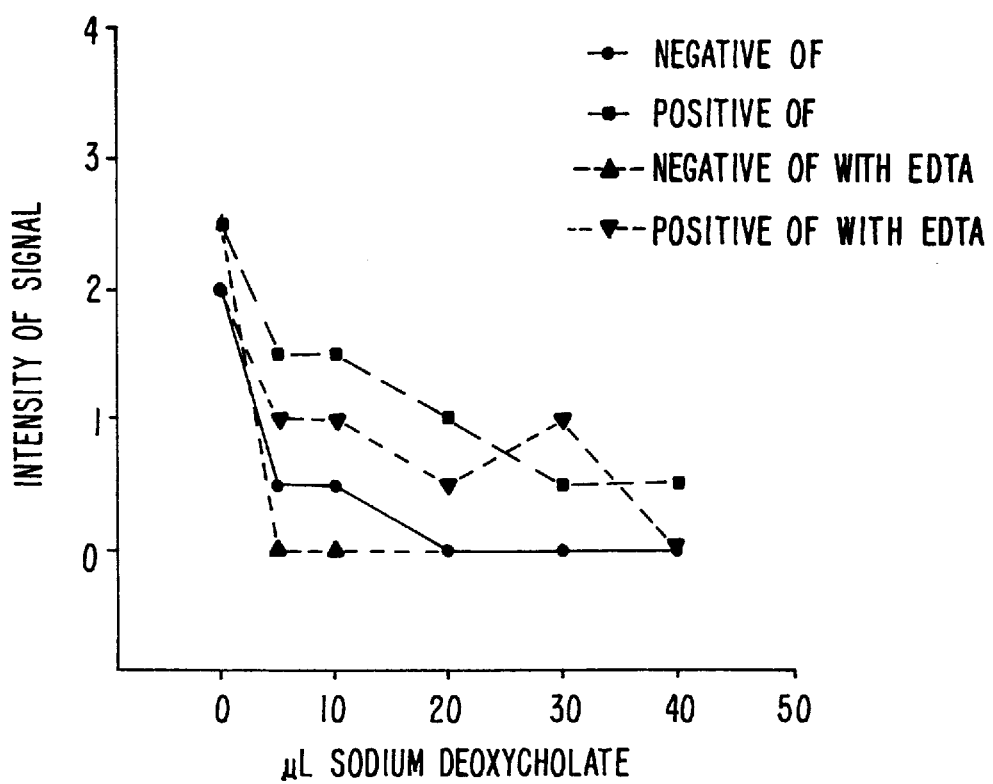
FIG. 4 shows a plot of signal intensity as a function of sodium deoxycholate concentration in HIV antibody negative and positive oral fluid samples assayed in a lateral flow immunochromatography assay.

This invention provides a novel method of reducing and/or eliminating the occurrence of false positives in oral-fluid based immunoassays, more preferably in immunoassays that utilize a particulate detectable label. The invention is based, in part, on the surprising discovery that the addition of a bile salt or acid to the oral fluid sample, prior to or during the assay, significantly reduces or eliminates the generation of false positive results. This is accomplished while retaining an acceptable level of true-positive signals thereby providing an immunoassay of greatly improved accuracy.

As shown by the data presented herein, the effect appears specific to bile salts and/or acids as conventional blocking agents such as non-ionic, cationic, zwitterionic, or other anionic surfactants do not provide the desired improvements in immunoassay results. These other surfactants typically either have no effect on the occurrence of false positives or, conversely, they depress the occurrence of true-positives to an unacceptable level.

In addition the data presented herein suggest the false positive signals observed in oral fluid based immunoassays are not mediated by IgG antibodies. This suggests that the bile salts or acids reduce the occurrence of false positives by a previously unknown mechanism.

In general, the methods of this invention involve providing an oral fluid sample for an immunoassay and combining that oral fluid sample with a bile salt or acid. As explained in detail below, the combination can be made before performing the immunoassay, simultaneously with application of the oral fluid sample to the immunoassay, or after the immunoassay commences.

It was also a surprising discovery of this invention that contacting the oral fluid with a chelator or sequester of divalent cations enhances the effect of the bile salt or acid on the occurrence of false positives. Thus, in another embodiment, the methods of this invention involve additionally contacting the oral fluid with a chelator of divalent cations or a sequestration agent. Detailed methods of practicing the methods of this invention are provided below.

I. Provision of an oral fluid sample combined with a bile salt/acid.

A) Collection of an oral fluid sample.

As explained above, the methods of this invention are directed to improvement of assays involving oral fluid, more preferably human oral fluid. The term "oral fluid", as used herein, refers to one or more fluids found in the oral cavity individually or in combination. These include, but are not limited to saliva and mucosal transudate. It is recognized that oral fluid (e.g., saliva) can comprise a combination of fluids from a number of sources (e.g., parotid, submandibular, sublingual, accessory glands, gingival mucosa and buccal mucosa) and the term oral fluid includes the fluids from each of these sources individually, or in combination. The term saliva refers to a combination of oral fluids such as is typically found in the mouth, in particular after chewing. The term "mucosal transudate", as used herein, refers to fluid produced by the passive diffusion of serum components from oral mucosal interstitia into the oral cavity. Mucosal transudate often forms one component of saliva.

The oral fluid can be collected by any of a number of means well known to those of skill in the art. Such means include, but are not limited to expectoration, mouth washes or rinse, absorbent sponges or pads, aspirators (e.g. syringes, straws, capillary tubes, and the like), chewable substrates (e.g., sponges, wax, or PARAFILM®), sour candies or fluids, and so forth. Indeed, a number of devices, fabricated expressly for sampling oral fluids, are commercially available (e.g. ORAQUICK® and ORASURE®, Oral Collection Devices by Epitope, Inc., Beaverton, Oreg., USA, RESOLVE® oral collection device by Osborn labs, OMNISAL® saliva collection system by Saliva Diagnostic Systems, Vancouver Wash., USA, etc.). See, also U.S. Pat. Nos. 5,022,409, 5,339,829, 5,335,673, 5,022,409, 5,112,758, 5,234,001, and 5,103,836.

Certain oral fluid collection devices are capable of concentrating (preferentially collecting) particular oral fluid components such as those bearing IgG antibodies (e.g. mucosal transudate). For example, one such device (the ORASURE® oral fluid collection device by Epitope, Beaverton, Oreg., USA) utilizes a salt-impregnated absorbent pad which is placed against the gums and cheek in the mouth. As the pad hydrates, the salts form a solution that is hypertonic to blood facilitating the transport of antibody-bearing transudate across the oral mucosa and into the collection device.

In a preferred embodiment where the analyte is an antibody or an antigen the oral fluid is collected using such a concentrating device and the transudate is concentrated to produce an average IgG or antigen concentration of at least about 1 $\mu$g/ml and more preferably at least about 2 $\mu$g/ml of the resulting oral fluid sample. In a particularly preferred embodiment, the oral fluid is concentrated to an IgG or antigen concentration averaging about 8 $\mu$g/ml in the resulting oral fluid sample.

Typically, the oral fluid specimen is collected according to the instructions provided for, or with, the particular collection means or device used. Thus, for example, in the case of the ORASURE® collection device, the collection pad is held against the gum and cheek until the pad absorbs oral fluid enriched for IgG. Typically this involves contact with the gum and cheek for about 2 minutes. The contact can be maintained up to about 5 minutes.

The collected oral fluid can be tested immediately or placed in a container for transport to a testing site. The oral fluid may be left "untreated" during storage and transport. Alternatively, the oral fluid sample can be combined with various "storage" solutions that may act as diluents, buffers, preservatives, and the like. The diluent can include the bile acids and/or chelating or calcium sequestration agents of this invention. The oral fluid alone, or in combination with the storage solution, can be desiccated or frozen for transport according to means well known to those of skill in the art.

In a particularly preferred embodiment, the oral fluid sample is collected and tested immediately (e.g., at the collection site) or within a relatively short time frame (e.g. several hours). In this embodiment, the oral fluid is most preferably collected with an oral fluid collection device such as the ORAQUICK® oral fluid collection device (Epitope Inc., Beaverton, Oreg., USA). This device comprises an absorbent pad (e.g., cotton or a sponge) affixed to the end of a plunger (e.g., a "syringe" plunger) which acts as a handle. The collection pad of the collector is placed in the mouth of the subject (preferably between cheek and lower gums) until the collection pad is loaded with oral fluid (in particular mucosal transudate); typically about 4 minutes.

The collector is then placed in a sample barrel (e.g., a syringe barrel) and the collection pad is compressed, by depression of the plunger, until the fluid coming out of the barrel adequately fills the sample well of the assay device, or other collection receptacle. In a most preferred embodiment the bile salt or acid, and optionally the chelator is automatically added to the sample, or the sample is optionally contacted with a sequesterer of divalent cations, as it is expelled from the barrel though a conditioning "filter" located in barrel tip. Detailed descriptions of such collection devices can be found in U.S. Pat. Nos. 5,339,829 and 5,479,937.

In general, the collection pad can be made of any of a number of absorbent materials suitable for oral use. Preferably, the pad is a thick, absorbent cotton roll or paper, such as commonly used in dental procedures. An example of such a pad is a 1.5 inch No. 2 medium cotton roll distributed by Patterson Dental Co. (Minneapolis, Minn., USA). Materials such as cellulose, polyurethane, polyester, and rayon are also useful.

In one embodiment of the invention, the pad is impregnated with one or more salts such that a hypertonic solution forms adjacent to or within the pad during use thereby enhancing the recovery of analyte. The salts are provided in an amount effective to recover a high concentration of test substance, such as immunoglobulin, in the oral fluid. As detailed in U.S. Pat. No. 5,103,836, the formation of a hypertonic solution results in a constant production of immunoglobulin from other sources within the oral cavity, those sources not being completely understood. By using creating a hypertonic solution, it is possible to gain an increase of as much as 8–16 times for immunoglobulin than by using distilled water.

A hypertonic solution is a salt solution which has an ionic strength exceeding that found in blood. In general, salts used in the preparation of the hypertonic solution of the present invention are present in an amount of from about 1.5% to about 5% by weight, preferably 3.5% by weight.

Salts which can be used in the preparation of the hypertonic solution include alkali metal compounds as well as alkaline earth metal compounds. Preferred salts include sodium chloride, potassium chloride, magnesium sulfate, magnesium chloride and calcium chloride. Sodium chloride is found to be the least toxic, least expensive and most palatable.

The hypertonic solution of the present invention can also include a compound or ingredient for stimulating salivation. The compounds capable of stimulating salivation are found to exhibit a sour taste. These compounds include weak organic acids. Preferred among the weak organic acids are citric acid, ascorbic acid and acetic acid. It is preferred to use citric acid and ascorbic acid at a concentration of between about 0.05% and 0.5% by weight. The preferable-range for acetic acid is between about 0.5% and 3.0% by weight.

In order to minimize degradation in a collected specimen, the absorbent pad or sponge can include a preservative. Such a preservative can act to inhibit proteolytic enzymatic activity which can be responsible for the destruction of antibody molecules. Compounds contemplated as a preservative include anti-bacterial agents, anti-fungal agents, bacteriostatic agents, fungistatic agents, and enzyme inhibitors. In one preferred embodiment benzoic acid, sorbic acid or the salts thereof are used as antifungal agents. As bacteriostatic agents, salts in high concentration and compounds capable of maintaining the hypertonic solution at low pH are contemplated. Such salts include thimerosal (or merthiolate), phenyl mercuric acetate, phenyl mercuric nitrate and sodium azide. Other preferred preservatives include preservatives which are typically used in medicines and mouthwashes. Examples include ethyl alcohol and chlorhexidine gluconate. Another class of preferred anti-microbial and anti-viral agents are detergents which can be used as topical germicides or in mouthwashes. An example is benzalkonium chloride. It is preferred to use these preservatives in a range of about 0.01% to about 0.2% by weight.

The pad is impregnated with the salt(s) by known means. A salt solution can be applied to the pad by dipping or spraying the pad so that the salts of the solution can be absorbed into and onto the pad which is then allowed to dry. Typically, the pad is dipped into a hypertonic solution and about 1 ml of solution is absorbed. Alternatively, a salt solution could be sprayed onto the pad until a sufficient amount, preferably about 1 ml is absorbed. Excess liquid is shaken off and the pad is placed in a forced-air, convection drying oven at 50° C. for 2 hours or, alternatively, in an oven at 80° C. for 6–12 hours in the absence of forced air.

Most materials from which the pad can be made can non-specifically bind protein. Thus, some immunoglobulins can undesirably bind to the pad and it is desired to block proteins from binding to the pad by using a blocking agent. To reduce non-specific binding in the collection of oral specimens, a blocking agent can be added to the hypertonic solution to be incorporated into the pad. A blocking agent is generally a soluble protein which is used to prevent non-specific binding of another protein to a solid surface. Compounds which can be added as blocking agents include albumin and gelatin, but any water soluble, non-toxic protein can be used as a blocking agent as long as the protein does not adversely affect the assay being used. It is preferred to use bovine gelatin. In general, blocking agents can be added to the salt solution used to impregnate the pad to form a hydrated concentration of between about 0.01% and 0.2% by weight. The contents of the hypertonic solution are then incorporated into the pad as described above. One preferred solution is described in U.S. Pat. No. 5,339,829.

As indicated above, a syringe or syringe-like device can be used to express the oral fluid sample from a collection sponge or absorbent pad. Such a device is illustrated in FIGS. 1A and 1B. With reference again to FIGS. 1A and 1B, syringe barrel 12 defines an inner wall 24 dimensioned lengthwise to receive the pad and plunger gasket, as shown in FIG. 2A, and in diameter, to snugly receive gasket 15, to form a fluid-tight seal therewith. The barrel has a flanged or radially enlarged opening 26 which facilitates placement of the pad, after oral-fluid-collection, into the barrel. The opposite, inner end of the barrel is provided with a frit 28 which acts as a fluid-permeable filter to allow passage of oral fluid absorbed in the pad to be expelled from the barrel, as the plunger is forced into the barrel. An outlet port 30 at the end of the barrel provides a socket for receiving cartridge 13. In an embodiment of the device which does not include cartridge 13, the outlet end of the barrel may be tapered to a narrow outlet, as in standard syringe construction. The syringe is also referred to herein as means for extracting oral fluid that has been absorbed into the pad.

Exemplary dimensions for the plunger-pad assembly and barrel according to the present invention are as follows. Plunger 11 is about 3 inches in length, including the length of sealing gasket 15, and about 0.12 inches in diameter. Absorbent pad 10 is about 1.5 inches in length and 0.375 inches in diameter. If a soft rubber gasket is used, a gasket diameter of 0.5 inches and a length of about 0.25 inches is appropriate to form a liquid-tight seal in a syringe barrel having an inner diameter of about 0.4375 inches.

Cartridge 13 includes an annular plug 32 which fits snugly into the socket in the barrel, to hold the cartridge firmly in the barrel. An interior passageway 33 through the chamber is provided with a reagent disc 34 impregnated with reagent (s) which are released into the oral fluid, preferably as solute components, when oral fluid is expelled through the cartridge. The reagent(s) can include a bile salt or acid a sequesterer of divalent cations, and reagents for use in detecting the target analyte(s) in the oral fluid, as discussed below. In addition, the reagent(s) may include a blocking agent such as gelatin, milk casein, or bovine serum albumin, suitable for use in certain types of solid-phase assays, also as discussed below. In one embodiment, a reporter-labeled antibody or antigen is dissolved at a concentration of a few mgs/ml in an aqueous solution containing 0.5% gelatin and 30% sucrose (to facilitate solubilization of protein when oral fluid passes through the cartridge). The reagent disk in the cartridge is sandwiched between fluid-permeable frits 35 and 36 in the cartridge chamber.

Additional embodiments for a cartridge and barrel are shown in FIGS. 3A and 3B. For example, as shown in FIG. 3A, a barrel outlet 38 can be a male Luer TM fitting 39 for attaching a corresponding female fitting 40 in a cartridge 42. The cartridge includes a rigid frit 44 impregnated with one or more reagent(s). A similar arrangement is shown in FIG. 3B except that the male Luer TM fitting 46 of a barrel outlet 48 is recessed in the body of the barrel. FIG. 3B also shows a barrel configuration in which the interior wall of the barrel is tapered on progressing toward its outlet end, to reduce the amount of oral fluid that remains in the barrel when the pad is compressed.

A strip 50 in the cartridge is a wettable reagent strip which, when wetted by oral fluids passing through the barrel, produces a detectable color change in the presence of analyte in the oral fluids. Analytes such as glucose can be detected using known enzymes, such as glucose oxidase coupled with a peroxidase system effective to produce a detectable color change in the presence of $H_2O_2$. In each of the cartridge embodiments illustrated in FIGS. 1–3, an interior chamber defines a passageway, such as the interior passageway 33 in cartridge 13, which may contain detection reagent(s) or reagent means effective to be released into the oral fluid when such is expelled from the barrel (FIGS. 1 and 2), or effective to mix with oral fluid passing through the passageway (FIG. 3).

Alternatively, the passageway containing the reagents may be contained in the outlet end of the barrel, e.g., along the side walls of a barrel outlet, avoiding the need for a separate cartridge. To collect a substance from the oral cavity with a collection device such as that illustrated in FIGS. 1A and 1B, the plunger-pad assembly is placed in the mouth of the patient such that the pad lies entirely within the mouth. Placement of the pad between the lower cheek and gums facilitates absorption of secretions originating from gingival lymphoid tissue as well as secretions from submucosal lymphoid tissue and salivary gland lymphoid tissue. After the pad has been impregnated with oral fluid, the pad is withdrawn from the mouth, and the plunger-pad assembly is placed in the syringe barrel pad-end-first so that oral fluid can be extracted from the pad.

The oral fluid can be stored for later analysis, preferably in a suitable preservation fluid. Alternatively, the oral fluid can be mixed with reagent(s) or expelled directly (without combination with reagents) or after mixing with reagents on a solid-phase detection device.

In another embodiment, the oral fluid is stored and/or transported after collection. In one such preferred embodiment, the oral fluid is collected with the ORASURE® collection device (Epitope Inc., Beaverton, Oreg., USA). The collected oral fluid is placed in a storage vial containing a storage solution. The storage solution comprises a preservative.

The oral fluid sample can be transported to the test site (e.g., laboratory) at ambient temperature via courier, air freight, or regular mail in accordance with applicable federal, state and local regulations regarding transportation of diagnostic specimens applicable to the subject analyte (e.g., HIV-1) oral sample specimens.

In a preferred embodiment, the oral fluid samples (on or off the collection pad) may be stored at 4° C. to 37° C. for a maximum of 21 days from the time of collection, including the time of shipping and testing. If testing of specimens cannot be completed within 21 days, the specimens can be stored frozen at −20° C. for a maximum of six additional weeks. Oral fluid samples frozen and thawed twice should be tested within 24 hours, or discarded.

One of skill will appreciate that these storage and handling conditions may vary with the collection and storage means. Typically, storage and handling will be performed in accordance with the recommendations of the manufacturers of the particular collection system utilized.

Once the oral fluid sample is transported to the testing site, the sample identification is recorded in accordance with standard protocols at the testing site and the oral fluid sample is verified that it is within acceptable dating for testing. The sample is then stored for subsequent testing or processed directly.

When the oral fluid sample is used for an assay, it is first extracted from the storage/transport device/media according to means appropriate for the particular storage/transport system used. Typically the sample will be removed according to methods recommended by the manufacturer of the particular collection system used. Thus, for example, where the collection system is the ORASURE® oral fluid collection device, the oral fluid will be removed from the storage tube by breaking the tip off of the transport tube and spinning the contained solution out of the transport tube into a centrifuge tube in a centrifuge at about 600–800×g force for 15 minutes.

In a particularly preferred embodiment, the sample will comprise a minimum of at least about 0.75 ml, more preferably about 1.0 ml volume. If the volume of the eluate (e.g. after centrifugation) is less than 0.75 ml, a new sample from the test subject should be obtained.

B) Combination of oral fluid sample with bile salt/acid.

The bile salt or acid can be combined with the oral fluid sample, typically at room temperature, before running the assay, simultaneously with application of the oral fluid to the assay device, or after application of the oral fluid to the assay. Thus, in one embodiment, the oral fluid sample is simply mixed with the bile salt or acid, alone or in combination with a buffer, prior to application to the assay. In another embodiment, the oral fluid can be applied to the assay device and then the bile salt or acid, or a diluent (e.g., buffer or other carrier fluid) containing the bile salt or acid, can be subsequently applied to the device thereby permitting mixture of the sample fluid and the bile acid in the assay device itself. Alternatively, the bile salt or acid and the oral fluid can be applied simultaneously to the assay device. In still yet another embodiment, the bile salt or acid or a diluent containing the bile salt or acid can be stored in a reservoir in the assay device. The bile salt or acid then combines with the oral fluid sample (i.e., in a mixing or combining chamber) after the oral fluid sample has been applied to the device.

Regardless of the means of combining, in a preferred embodiment, the bile salt is provided in an amount such that the final concentration of the bile salt in the oral fluid in the assay ranges from about 0.1 weight percent to about 1 weight percent, more preferably from about 0.3 weight percent to about 0.6 weight percent, and most preferably from about 0.45 weight percent to about 0.55 weight percent of the solution applied to the assay.

Where a diluent is provided, suitable diluents are chosen to be compatible with the analyte and with the target antibodies and/or proteins in the subject assay. Typically the diluents are chosen to avoid denaturation or other degradation of the proteins or antibodies and to provide a milieu compatible with and facilitating of antibody/target (epitope) binding. While any diluent typically used in immunoassays is suitable (See, e.g., *Current Protocols in Immunology* Wiley/Greene, NY; Harlow and Lane (1989); *Antibodies: A Laboratory Manual,* Cold Spring Harbor Press, NY; Stites et al. (eds.) *Basic and Clinical Immunology* (4th ed.) Lange Medical Publications, Los Altos, Calif., and references cited therein), a particularly preferred diluent comprises 0.1M $NaHCO_3$, pH 8.0. A preservative can also be added (e.g., about 0.01% thimerosal). Particularly preferred diluents are buffers ranging from about pH 7 to about pH 9, more preferably from about pH 7.5 to about pH 8.5, and most preferably around pH 8.

One of skill in the art will appreciate that the diluent (sample buffer) can additionally include a protein or other moiety unrelated to the analyte which participates in non-specific binding reactions with the various components of the assay (e.g., the substrate) and thereby blocks and prevents non-specific binding of the anti-HIV-1 or the labeled anti-human antibodies. A particularly preferred blocking agent is bovine serum albumin (BSA) or polyvinyl alcohol (PVA).

In one embodiment, the oral fluid sample is diluted at a diluent:sample ratio ranging from about 1:1 up to about 1:20 (v/v), more preferably from about 1:1 up to about 1:15 (v/v) and most preferably from about 1:1 up to about 1:10 (v/v). In one particular preferred embodiment, the sample is diluted at a diluent:sample ratio of about 1:8 (v/v). In certain embodiments, the oral fluid sample may not be diluted at all prior to use.

II. Bile salts/acids.

It was a discovery of this invention that combination of bile salts, and/or their corresponding acids (bile acids), with oral fluid samples greatly reduces and/or eliminates the occurrence of false positives in oral-fluid based assays that utilize a particulate moiety as a detectable label. Bile acids are acids that are synthesized in the liver and function to facilitate the absorption of dietary triacylglycerols and fat-soluble vitamins. Naturally occurring bile acids are the end products of cholesterol metabolism. Primary bile acids are those that are synthesized in hepatocytes directly from cholesterol. The most abundant bile acids in humans are derivatives of cholanic acid (Formula I), that

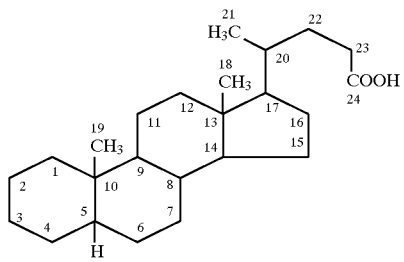

is cholic acid and chenodeoxycholic acid. The primary bile acids are composed of 24 carbon atoms, contain two or three OH groups and have a side chain that ends in a carboxyl group that is ionized at pH 7.0. The carboxyl group of the primary bile acid is often conjugated via an amide bond to either glycine ($NH_2$—$CH_2$—COOH) or taurine ($NH_2$—$CH_2$—$CH_2$—$SO_3H$) to form glycocholic or taurocholic acid, respectively.

When primary bile acids undergo further chemical reactions, e.g., by microorganisms in the gut, they give rise to secondary bile acids that also possess 24 carbon atoms. Examples of secondary bile acids include, but are not limited to cholic acid (or cholate salt) deoxycholic acid (or deoxycholate salt) and lithocholic acid (or lithocholate salt), which are derived from cholic acid and chenodeoxycholic acid respectively by the removal of one OH group. Other bile acids include, but are not limited to ursodeoxycholic acid, glycodeoxycholic acid, taurodehydrocholic acid, and taurodeoxycholic acid.

The term bile acid is used herein to include naturally occurring primary and secondary acids, purified bile acids, and bile acids that are synthesized chemically, or biologically (e.g., by cells in culture), or recombinantly (by recombinantly transformed cells, tissues, or organisms). Bile acids or their salts also include substituted and conjugated bile acids and salts comprising functionally equivalent analogues of deoxycholate or the other bile acids indicated herein as being effective in reducing false positives in immunoassays utilizing particulate indicators as detectable labels. Such substituted and/or conjugated bile acids and their salts can include, but are not limited to nor-bile acid derivatives (see, e.g., U.S. Pat. No: 5,512,558), tetrazole derivatives (see, e.g., U.S. Pat, No. 5,466,815), polymers and oligomers of bile acid derivatives (see, e.g., U.S. Pat. No. 5,430,116), fluorinated bile acid derivatives (see, e.g., U.S. Pat. No. 5,175,320, 5,061,701), homo-derivatives, bishomo-derivatives, trishomo-derivatives, alpha-carboxy-homo-, alpha-carboxy-bishomo-derivatives, phosphate derivatives, alpha-hydroxyl-derivatives, nitrogen containing side chain derivatives, and L-aspartate, L-glutamate, L-lysine, R-phenylglycine, 12-aminododecanoic acid and 4-aminohippuric acid conjugate derivatives of cholic, deoxycholic, chenodeoxycholic, ursodeoxycholic, lithocholic, and other bile acids (see, e.g., U.S. Pat. No. 5,541,348). One of skill will appreciate that the terms bile salt and bile acid are used interchangeably herein recognizing that at a particular pH, the bile acid will deprotonate thereby producing the corresponding salt.

The "naturally occurring" and modified bile acids or salts of this invention can be produced by any of a wide variety of methods well known to those of skill in the art. These include isolation from animal sources (e.g., animal tissues), de novo chemical syntheses, chemical modification of isolated bile salts, expression of bile salts in cell and/or tissue culture, expression of bile salts in recombinantly transformed cells, tissues, or organisms, and chemical modification of such expressed bile salts. Methods of producing naturally occurring and/or chemically modified bile salts (acids) can be found, for example, in U.S. Pat. Nos. 5,541,348, 5,512,558, 5,510,114, 5,466,815, 5,462,933, 5,430,116, 5,428,182, 5,362,891, 5,352,682, 5,250,524, 5,175,320, 5,166,374, 5,096,898, 5,079,240, 5,061,701, 5,057,509, 4,834,919, 4,810,422, 4,793,948, 4,388,241, 4,025,987, 3,931,256, 3,919,266, 3,910,888, and 3,846,411. Methods of extraction of the basic cholic acid component of the bile acids of this invention are described by Wieland (1939) Z. Physiol. Chem., 262: 1, and by Gattermann-Wieland (1961), at page 360 In: Praxis des Organischen Chemikers, de Gruyter, Berlin, $40^{th}$ Ed.). The chemical synthesis is described by Fieser (1959) In: Steroids, Fieser, ed., Reinhold, N.Y. In addition, a large number of bile salts are commercially available (see, e.g., Aldrich Chemical Co., Inc., Milwaukee, Wis., USA, Sigma Chemical Co., Inc., St. Louis Mo., USA, etc.).

III. Identification of functionally equivalent bile salts/acids.

As explained above, bile salts or acids suitable for practice of this invention include any of the primary or secondary bile salts, modified (substituted or otherwise conjugated) primary or secondary bile salts or acids, and functionally equivalent analogues thereof.

Functionally equivalent analogues can be identified simply by routine screening. A functionally equivalent analogue refers to an analogue of a bile salt or acid that, when combined with an oral fluid sample, significantly reduces the incidence of false positives in an immunoassay that utilizes a particulate, or microparticulate, label (e.g., in a lateral flow immunochromatography assay) as compared to the same oral fluid sample lacking the bile salt or acid when tested in the same assay.

Thus, functionally equivalent analogues can be identified simply by screening an oral fluid sample known to be positive or negative for a particular analyte (e.g., HIV antibody) with and without the bile salt analogue in question. The number of false positives and false negatives can be determined. The question of whether or not the bile salt analogue significantly decreases the number of false negatives can be determined by statistical analyses well known to those of skill in the art (e.g., analysis of variance (ANOVA), pairwise T-test, etc.). Screening of a bile salt and determination of the number of false positives and false negatives is illustrated below in Example 1.

It is recognized that the pH, particular type of bile salt, and optimal concentration of bile salt combined with the oral fluid will vary with the type of oral fluid sample, the collection method, the subject analyte, and the particular assay used to detect the analyte. One of skill will appreciate that the above-described approach is used to optimize the pH of the diluent or assay, and the type or amount of bile salt or acid added to the oral fluid sample to achieve optimal results in any particular assay. Thus, in order to optimize the bile salt concentration, a series of assays are run using the particular collection method and/or the particular assay method or device of interest while varying the pH and/or type and/or amount of bile salt or acid combined with the oral fluid sample. The frequency of false positives and negatives can be determined as a function of bile salt concentration and the bile salt concentration providing the best combination of low false positives and high detection rate (low false negatives) is selected.

For example, the experiments reported in Table 4 (Example 4) indicate that ursodeoxycholate made the oral fluid sample to viscous to flow in the particular Chembio assay device. However, it is known that bile salts (or acids) tend to form large micelles and aggregate at low pH thereby increasing the viscosity of the sample. It is expected that an increase in pH (e.g., to pH 8.5 or pH 9.0) would reduce the viscosity of the oral fluid sample containing ursodeoxycholate. Similarly, it is expected that reducing the ursodeoxycholate concentration would similarly decrease viscosity. The ursodeoxycholate pH and concentration could be optimized by a series of experiments systematically varying the pH and/or the concentration of the bile salt, as described above and in Examples 1 and 6, to identify the concentration and pH that provides the most effective results using ursodeoxycholate.

IV. Chelator of Divalent Cations.

It was also a discovery of this invention that combination of a divalent cation chelator with the oral fluid sample, or contact of the oral fluid sample with a composition that binds or sequesters divalent cations, improves the effectiveness of the bile salt or acid in reducing the incidence of false positives. Thus, for example in one preferred embodiment, the oral fluid is treated by addition of a bile salt (e.g., sodium deoxycholate) and a divalent cation chelator or sequestration agent such as EDTA.

The chelator can be combined with oral fluid sample before, during, or after addition of the bile salt or acid to the oral fluid. Thus, for example, the chelator can be provided in the storage and/or preservation fluid provided with an oral fluid collection device. The chelator is then combined with the oral fluid during storage and transport. Alternatively, the chelator can be combined with the oral fluid just before application of the oral fluid sample to the assay device. In yet another embodiment, the chelator can be added to the assay device after application of the oral fluid or it can be stored in a reservoir within the assay device.

In a preferred embodiment, the chelator is provided in an amount such that the chelator comprises about 0.001M to about 0.05M, more preferably from about 0.005M to about 0.02M, and most preferably from about 0.008M to about 0.012M of the final chelator/oral fluid/bile salt/(optional) buffer solution.

In another embodiment, the chelator need not be combined, but only contacted with the oral fluid and/or the oral fluid/bile salt mixture. Thus, for example where the immunoassay involves progression of the fluid through a porous matrix, the matrix material itself can be made of a material that chelates or otherwise sequesters or binds to divalent cations. Such matrix materials are well known to those of skill in the art. The most common sequestration agents are often used as ion exchange resins and include, but are not limited to chelex resins containing iminodiacetate ions, or resins containing free base polyamines, or aminophosphonic acid. Alternatively, the oral fluid or oral fluid/bile salt mixture can be pretreated by passage through a matrix that chelates or otherwise sequesters divalent cations. This pretreatment can be incorporated into the storage and transport container, provided as filtration step, or provided as a component of the method of extraction of the oral fluid sample from the collection device. In this latter embodiment, for example, centrifugation of the oral fluid sample out of the collection device can entail passage of the oral fluid through a chelation or sequestration matrix in route to a collection chamber which may or may not itself be provided as a component of the immunoassay device.

In a preferred embodiment, the oral fluid or oral fluid/bile salt mixture can be pretreated by passage through a chelating matrix as it passes out of the oral fluid collection device (e.g., ORAQUICK®, Epitope, Inc., Beaverton, Oreg., USA) into the assay device (e.g., a rapid assay device such as the HIV1/2 Stat-Pak Ultra Fast HIV Assay, Chembio Diagnostic Systems, Medford, N.Y.).

V. Suitable assays for the practice of this invention.

The methods of this invention are practicable with essentially any assay that uses a particulate moiety as a detectable label. The term particulate moiety is used to refer to any element or compound that is insoluble in the particular buffer system of the immunoassay in which it is utilized or which precipitates out of solution to form a detectable moiety. Typically particulate labels are detected (i.e., recognized as producing a "signal") when they accrete, agglutinate, or precipitate out of solution to form a detectable mass (distinguishable from the non-accreted, agglutinated or solubilized form of the "particle"), most preferably in a discrete region of the assay medium. Microparticles or "microparticulate labels" are particles or labels ranging in size from about 0.1 nm (average diameter) to about 1000 nm, preferably from about 1 nm to about 1000 nm, more preferably from about 10 nm to about 100 nm, and most preferably from about 15 nm to about 25 nm. Preferred particulate labels include, but are not limited to, particles such as charcoal, kolinite, bentonite, red blood cells (RBCs), colloidal gold, clear or colored glass or plastic (e.g. polystyrene, polypropylene, latex, etc.) beads or microspheres.

Assays, in particular immunoassays, that utilize particulate moieties as detectable labels are well known to those of skill in the art. Such assays include, but are not limited to fluid or gel precipitin reactions, agglutination assays, immunodiffusion (single or double), immunoelectrophoresis, immunosorbent assays, various solid phase assays, immunochromatograpy (e.g., lateral flow immunochromatography) and the like. Method of performing such assays are well known to those of skill in the art (see, e.g., U.S. Pat. Nos. 4,366,241; 4,376,110; 4,517,288; 4,837,168; 5,405,784; 5,534,441; 5,500,187; 5,489,537; 5,413,913; 5,209,904; 5,188,968; 4,921,787; and 5,120,643; British Patent GB 2204398A; European patent EP 0323605 B1; Methods in Cell Biology Volume 37: *Antibodies in Cell*

*Biology*, Asai, ed. Academic Press, Inc. New York (1993); and *Basic and Clinical Immunology* 7th Edition, Stites & Terr, eds. (1991)).

VI. Target analyte.

The particular target analyte of the assay is not critical to the invention. Suitable analytes include virtually any analyte found in mammalian, more preferably rodent, largomorph, bovine, equine, canine, feline, porcine, primate, and human oral fluid. Virtually any analyte that can be suspended or dissolved in an aqueous solution can be detected using the methods of this invention. Examples of analytes of interest include 1) antibodies such as antibodies to HIV (e.g., HIV-1 and HIV-2), HTLV (e.g., HTLV-1, HTLV-2), *Helicobacter pylori*, hepatitis (e.g., hepatitis A, B and C), measles, mumps, and rubella; 2) drugs of abuse and their metabolic byproducts such as cotinine, cocaine, benzoylecgonine, benzodizazpine, tetrahydrocannabinol, nicotine, ethanol; 3) therapeutic drugs including theophylline, phenytoin, acetaminophen, lithium, diazepam, nortryptyline, secobarbital, phenobarbitol, theophylline, and the like; 4) hormones and growth factors such as testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, IGA and sex hormone binding globulin; and 5) other analytes including glucose, cholesterol, caffeine, cholesterol, corticosteroid binding globulin, DHEA binding glycoprotein, and the like.

VII. Kits for the detection of an analyte in oral fluid.

In another embodiment, this invention provides kits for the detection of an analyte in an oral fluid sample. In a preferred embodiment, the kits include a reagent comprising a bile salt and/or acid and a means for performing an immunoassay utilizing a particulate moiety as a detectable label. The kits can additionally include a means for collecting an oral fluid sample. The kits can also include instructional materials describing the use of the assay and/or the oral collection means. The instructional materials can additionally describe the use of the bile salt or acid in the assay.

The bile salt or acid can be one or more of the bile salts or acids described herein. Similarly, the means for collecting an oral fluid sample can include any of the means described herein, with an oral fluid collection device such as the ORAQUICK® oral fluid collection device (Epitope Inc., Beaverton, Oreg., USA) being most preferred (see, e.g., U.S. Pat. Nos. 5,339,829 and 5,479,937). The means for performing an immunoassay utilizing a particulate moiety as a detectable label can include, but is not limited to, any of the above-described immunoassays, with rapid assays, more preferably lateral flow immunochromatography assays such as the HIV 1/2 Stat-Pak Ultra Fast HIV Assay (Chembio Diagnostic Systems, Medford, N.Y.) being most preferred. The assay can be selected to detect virtually any analyte, preferably any of the analytes described herein, more preferably an analyte that is an antibody to, or an antigen of, an infectious disease agent, and most preferably an antibody to or an antigen of HIV.

The kit can of course include appropriate packaging, containers, labeling, buffers, controls and indicators for determining positive and negative results.

EXAMPLES

The following examples are offered to illustrate, but not to limit the present invention.

Example 1

As indicated above, this invention is based, in part, on the discovery that combination of an oral fluid sample with a bile salt or acid diminishes the occurrence of false positives in immunoassays designed to detect an analyte within that oral fluid sample. This example illustrates the effect of a bile salt on the occurrence of false negatives in one such immunoassay.

Preparation of the ChemBio HIV Assay.

The ChemBio HIV assay (Chembio HIV 1/2 Stat-Pak Ultra Fast assay, Chembio Diagnostic Systems, Medford, N.Y., USA) uses an 8×56 mm plastic backed nitrocellulose strip with an 8×17 mm polyester sample application pad at one end. Approximately 5 mm of the sample application pad protrudes over the edge of the nitrocellulose strip, so that the pad covers the first 12 mm of the nitrocellulose strip.

A line of approximately 1 μg of recombinant HIV antigen is placed at approximately the 15 mm point on the strip (measured from the proximal end) and a control line of goat anti-human antibody at approximately the 27 mm point on the strip.

In manufacture, the sample application pad is soaked in a 50 mM sodium phosphate solution (pH 7.4) containing 0.5% bovine serum albumin (BSA), 0.5% (PVA), 0.1% Triton X-100. The pad is then dried by lyophilization. A solution of colloidal gold is prepared by standard techniques (Ching et al. U.S. Pat. No. 5,120,643) and diluted approximately 1/30 to a final solution containing 0.7% sucrose and 0.17% trehalose. Three microliters of this solution is deposited on the sample application pad (attached to the nitrocellulose strip and containing the desired solution of BSA, PVA, and Triton X-100). The strip and pad assembly is again dried leaving a deposition of dried colloidal gold on the sample pad.

Effect of bile salt/acid on assays.

Data illustrating the advantageous effect of the inclusion of a bile salt, in particular deoxycholate, in the oral sample before application to the sample pad of the ChemBio strip is shown in FIG. 4. Six two hundred microliter samples of HIV antibody negative oral fluid were collected with PVA sponge pads (Kanebo Corp., Japan). Each oral fluid sample was filtered through Schleicher and Schuell filter paper (GelBlot2 grade), and then 0, 5, 10, 20, 30, or 40 ml volumes of 10% deoxycholate were added to the series of six samples.

The samples were then run on the ChemBio strips (in duplicate), using standard volumes recommended by the manufacturer, and the test lines were rated on a scale of 0 to +3 (strongest signal). Identical sample runs were prepared, but a sample of HIV positive serum was added to each at a final dilution of 1:10,000. This series of six "HIV positive" oral fluid samples was also run on the ChemBio strips in duplicate. An additional series of 6 negative and 6 positive samples was prepared, but with the addition of 10 μL of 0.2M EDTA to all samples. The results are shown in FIG. 4 and in Table 1 below.

TABLE 1

Effect of deoxycholate, with and without EDTA, on false positives and false negatives in lateral flow immunochromatography assay of oral fluid.

| Strip | deoxy-cholate μl | Buffer μl | Without EDTA | | With 10 μl EDTA | |
| --- | --- | --- | --- | --- | --- | --- |
| | | | Negative | Positive | Negative | Positive |
| Test | 0 | 0 | 2 | 2.5 | 2.5* | 2 |
| Control | 0 | 0 | 3 | 3 | 3* | 3 |
| Test | 0 | 30 | 1.5 | 2 | 2.5 | 2 |
| Control | 0 | 30 | 3 | 3 | 3 | 3 |
| Test | 5 | 30 | 0.5 | 1.5 | 0 | 1 |
| Control | 5 | 30 | 3 | 3 | 3 | 3 |
| Test | 10 | 30 | 0.5 | 1.5 | 0 | 1 |

TABLE 1-continued

Effect of deoxycholate, with and without EDTA, on false positives and false negatives in lateral flow immunochromatography assay of oral fluid.

| Strip | deoxy-cholate μl | Buffer μl | Without EDTA Negative | Without EDTA Positive | With 10 μl EDTA Negative | With 10 μl EDTA Positive |
|---|---|---|---|---|---|---|
| Control | 10 | 30 | 3 | 3 | 3 | 3 |
| Test | 20 | 30 | 0.005 | 1 | 0 | 0.5 |
| Control | 20 | 30 | 3 | 3 | 3 | 3 |
| Test | 30 | 30 | 0 | 0.5 | 0 | 1 |
| Control | 30 | 30 | 3 | 3 | 3 | 3 |
| Test | 40 | 30 | 0 | 0.5 | 0 | 0.005 |
| Control | 40 | 30 | 3 | 3 | 3 | 3 |

*No EDTA control.

As can be seen in FIG. 4, HIV antibody-negative oral fluid (OF) gave a false-positive signal (+2) without addition of deoxycholate. This false-positive signal rapidly declined as deoxycholate was added (false positive signal of 0 with 20 μl of deoxycholate). A true positive sample (1:10,000) dilution of positive serum in HIV antibody negative oral fluid) gave a signal of +1 with 20 μl of added deoxycholate. The addition of 10 μl of 0.2M EDTA to oral fluid samples lowered the amount of deoxycholate needed to obtain a zero signal to 10 μl.

Example 2
Comparison of Deoxycholate to SDS

Figure 5:
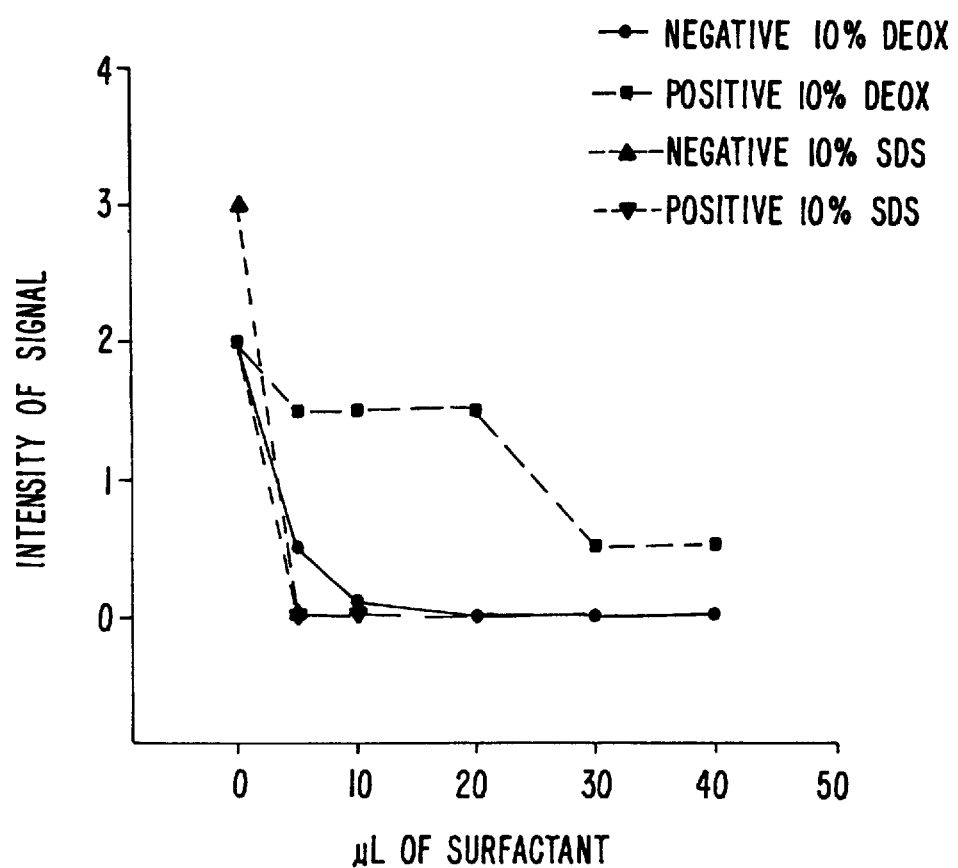
FIG. 5 shows a plot of signal intensity as a function of deoxycholate or sodium dodecyl sulfate concentration in HIV antibody negative and positive oral fluid samples in a lateral flow immunochromatography assay.

A similar experiment was also performed comparing the addition of 10% deoxycholate and 10% sodium dodecyl sulfate (SDS). As seen in Table 2 and FIG. 5, the addition of SDS, unlike deoxycholate, eliminated false positive and true positive signals at the same concentration.

TABLE 2

Comparison between sodium deoxycholate and sodium dodecyl sulfate.

| | 10% Deoxycholate μl | Negative | Positive | 10% SDS μl | Negative | Positive |
|---|---|---|---|---|---|---|
| Test | 0 | 2 | 2 | 0 | 3 | 2 |
| Control | 0 | 3 | 3 | 0 | 3 | 3 |
| Test | 5 | 0.5 | 1.5 | 5 | 0.005 | 0.005 |
| Control | 5 | 3 | 3 | 5 | 3 | 3 |
| Test | 10 | 0.1 | 1.5 | 10 | 0 | 0.005 |
| Control | 10 | 3 | 3 | 10 | 2.5 | 2 |
| Test | 20 | 0.005 | 1.5 | 20 | 0 | 0 |
| Control | 20 | 3 | 3 | 20 | 2 | 1 |
| Test | 30 | 0 | 0.5 | 30 | 0 | 0 |
| Control | 30 | 3 | 3 | 30 | 0.5 | 0.005 |
| Test | 40 | 0 | 0.5 | 40 | 0 | 0 |
| Control | 40 | 3 | 3 | 40 | 0.005 | 0 |

Example 3

Comparison of Deoxcholate to Other Detergents.

Figure 6:
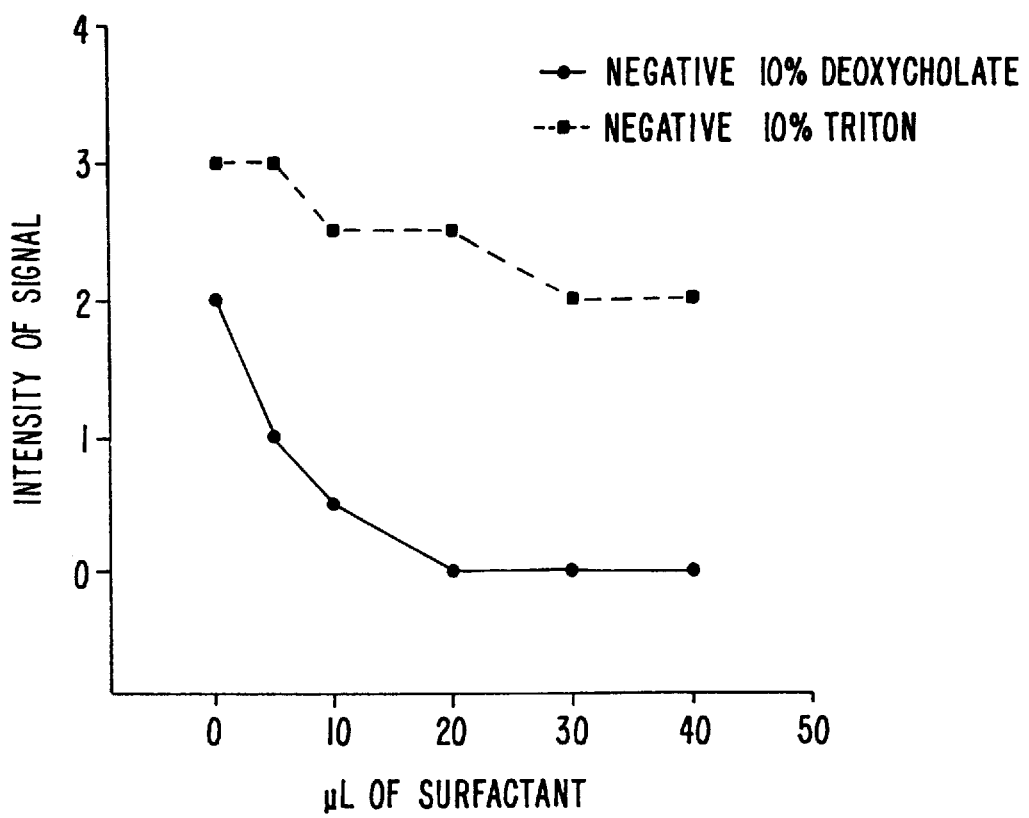
FIG. 6 shows a plot of signal intensity as a function of deoxycholate or Triton X-100 concentration for HIV antibody negative oral fluid samples in a lateral flow immunochromatography assay.

A number of other detergents were tested under similar experimental situations. FIG. 6 and Table 3 show the results obtained when parallel experiments were run with the non-ionic detergent Triton X-100.

TABLE 3

Comparison of Deoxycholate with Triton X-100.

| | 10% Deoxycholate μl | Negative | 10% Triton X-100 μl | Negative |
|---|---|---|---|---|
| Test | 0 | 2 | 0 | 3 |
| Control | 0 | 3 | 0 | 2 |
| Test | 5 | 1 | 5 | 3 |
| Control | 5 | 3 | 5 | 3 |
| Test | 10 | 0.5 | 10 | 2.5 |
| Control | 10 | 3 | 10 | 3 |
| Test | 20 | 0.005 | 20 | 2.5 |
| Control | 20 | 3 | 20 | 3 |
| Test | 30 | 0 | 30 | 2 |
| Control | 30 | 3 | 30 | 3 |
| Test | 40 | 0 | 40 | 2 |
| Control | 40 | 3 | 40 | 3 |

As shown below in Table 4, only detergents related to the bile salts were effective in eliminating the false positive reactions with oral fluid samples in the lateral flow microparticle immunoassay.

TABLE 4

Comparison of bile salts to non-ionic, zwitterionic, cationic, and other anionic surfactants.

| Detergent | Effect on false Positive | Effect on true positive |
|---|---|---|
| NON-IONIC | | |
| 2% Tween-20 | no effect | some reduction |
| 10% Triton X-100 | small reduction | some reduction |
| ZWITTERIONIC | | |

TABLE 4-continued

Comparison of bile salts to non-ionic, zwitterionic, cationic, and other anionic surfactants.

| Detergent | Effect on false Positive | Effect on true positive |
|---|---|---|
| 10% CHAPS* | no effect | some reduction |
| ANIONIC | | |
| 10% SDS | eliminated | eliminated |
| 10% Na deoxycholate | eliminated | no effect |
| 10% Na cholate | 95% reduction, but | |

TABLE 4-continued

Comparison of bile salts to non-ionic, zwitterionic, cationic, and other anionic surfactants.

| Detergent | Effect on false Positive | Effect on true positive |
|---|---|---|
| 10% Na chenodeoxy-cholate | less than deoxycholate at same concentration eliminated | no effect |
| 10% glycodeoxycholate | eliminated | slight reduction, more than Na deoxycholate |
| 10% ursodeoxycholate | made sample too viscous to flow | |
| 10% Na taurodeoxy-cholate | reduced, but less so than with deoxycholate | no effect |
| CATIONIC | | |
| cetylpyridinium chloride | strong increase | |

*CHAPS is 3-[3-Cholamidopropyldimethylammonio)-1-propanesulfonate

Example 4
Chelators of Divalent Cations Potentiate the Effect of Bile Salts

As indicated in Table 1, EDTA potentiates the effect of deoxycholate in reducing false positive reactions. Although the mechanism for this is unknown, it is a reasonable that it may be due to complexing of divalent cations such as calcium. Calcium occurs in relatively high concentration in saliva, and may facilitate the non-specific binding of proteins through ionic bridges.

Sodium citrate, a compound that also complexes with calcium, albeit with lower affinity, was therefore also tested. Like EDTA, sodium citrate potentiates the ability of deoxycholate to reduce false positive reactions in this immunoassay system.

Example 5
False Positive Signals Are Not Dependent on IgG in Sample

In order to evaluate whether or not the false positive signal was dependent on the presence of IgG in the oral fluid samples, IgG was removed by adsorption with solid-phase protein A. Adsorption with protein A does not remove the false-positive signal. In addition, the false-positive signals obtained with IgG-depleted oral fluid were eliminated with deoxycholate/EDTA in the usual manner.

Example 6
Optimization of Bile Salt and Chelator

In order to determine optimum concentrations of deoxycholate and EDTA, preclinical trials were performed. Determination of optimum concentration was desired because the concentration of mucopolysaccharides and other oral fluid components vary considerably from person to person, with collection method, and even from sample to sample from the same person. Data from the most recent trial is shown below in Table 5.

TABLE 5

Data from preclinical trial of immunoassay method.

| Subject | Serostatus | Rapid Assay Result with EDTA | Rapid Assay Result with citrate |
|---|---|---|---|
| 24340 | neg | +1 | +1 |
| 24341 | neg | IV | IV |
| 44010 | neg | 0 | +0.5 |

TABLE 5-continued

Data from preclinical trial of immunoassay method.

| Subject | Serostatus | Rapid Assay Result with EDTA | Rapid Assay Result with citrate |
|---|---|---|---|
| 31594 | neg | 0 | 0 |
| 24348 | neg | 0 | 0 |
| 31620 | neg | 0 | +0.5 |
| 44009 | neg | 0 | 0 |
| 31621 | neg | 0 | +1 |
| 15491 | pos | +2.5 | +2 |
| 31641 | pos | +1.5 | +1.5 |
| 44006 | neg | 0 | 0 |
| 24353 | neg | 0 | 0 |
| 24332 | pos | +2 | Ind. |
| 31646 | pos | +1 | Ind. |
| 15499 | pos | +3 | +1 |
| 24321 | neg | 0 | 0 |
| 15473 | pos | IV | Ind. |
| 15472 | pos | +3 | +3 |
| 24384 | pos | +2 | +2 |
| 31642 | neg | 0 | 0 |
| 15495 | pos | +2 | +1 |
| 15428 | pos | +3 | +2 |
| 15425 | pos | +2 | +1 |
| 31588 | pos | +1 | +1 |
| 24347 | neg | 0 | 0 |
| 15441 | pos | +2 | +2 |
| 24357 | neg | 0 | Ind. |
| 15496 | pos | +2 | +2 |
| 44008 | neg | 0 | 0 |
| 44007 | neg | +0.5 | Ind. |
| 31573 | pos | +3 | +2 |

In sum, with 32 subjects whose oral fluid samples were preconditioned by treatment with deoxycholate and EDTA (30 µL 10% deoxycholate, 10 µL 0.2M EDTA), the sensitivity was 100%, the specificity was 87% with two subjects giving samples of insufficient volume (IV). Without the use of deoxycholate, the specificity was typically near zero i.e., all HIV antibody negative subjects gave false-positive reactions.

A total of three such trials have been run (using deoxycholate/EDTA sample conditioning) as summarized in Table 6 below.

TABLE 6

Summary of preclinical trials.

| Trial | True negative | Rapid Assay Negatives | True Positives | Rapid Assay Positives |
|---|---|---|---|---|
| Thailand | 10 | 10 | 10 | 10 |
| 1st In-house | 16 | 15 | 12 | 11 |
| 2nd In-house | 15 | 13 | 14 | 14 |
| Total | 41 | 38 | 36 | 35 |

Overall sensitivity = 97.2%
Overall specificity = 92.7%

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of reducing false positives in assays for the detection of an analyte in an oral fluid sample, said method comprising the step of providing an oral fluid sample combined with a bile acid bile or salt; wherein said bile acid bile or salt is present in a concentration sufficient to reduce the rate of occurrence of false positives in said assays; and wherein said assays are characterized by the use of a particulate moiety as a detectable label.

2. The method of claim 1, wherein said bile acid bile or salt is selected from the group consisting of deoxycholic acid (deoxycholate salt), cholic acid (cholate salt), chenodeoxycholic acid (chenodeoxycholate salt), glycodeoxycholic acid (glycodceoxycholate salt), and taurodeoxycholic acid (taurodeoxycholate salt).

3. The method of claim 2, wherein said bile acid or bile salt is deoxycholic acid or deoxycholate salt.

4. The method of claim 1, wherein said bile acid or bile salt ranges in concentration from about 0.1 weight percent to about 1.0 weight percent of the oral fluid/bile salt or bile acid combination.

5. The method of claim 1, further comprising contacting a chelator of divalent cations with said oral fluid sample.

6. The method of claim 5, wherein said chelator is selected from the group consisting of EDTA, EGTA, NTA, CDTA, sodium citrate, and a chelating resin.

7. The method of claim 6, wherein said chelator is EDTA.

8. The method of claim 1, wherein said assay is an immunoassay that use a particulate detectable label.

9. The method of claim 8, wherein said assay is an immunochromatography assay.

10. The method of claim 1, wherein said providing comprises using a collection means selected from the group consisting of a sponge, an absorbent pad, a salt-impregnated absorbent pad, an aspirator, and a mouth rinse to collect said oral fluid sample.

11. The method of claim 1, wherein said oral fluid sample is predominantly mucosal transudate.

12. The method of claim 1, wherein said analytes are selected from the group consisting of antibodies to antigens of infectious diseases, antigens of infections diseases, hormones, growth factors, therapeutic drugs, drugs of abuse and products of the metabolism of drugs of abuse.

13. The method of claim 12, wherein said antigens are antigens of hepatitis B and said antibodies are selected from the group consisting of antibodies to HIV, antibodies to HTLV, antibodies to *Helicobacter pylon*, antibodies to hepatitis, antibodies to measles, antibodies to mumps, and antibodies to rubella.

14. The method of claim 13, wherein said analyte is an antibody to HIV.

15. The method of claim 12, wherein said therapeutic drugs and drugs of abuse or products of the metabolism of drugs of abuse are selected from the group consisting of tetrahydrocannabinol, nicotine, ethanol, theophylline, phenytoin, acetaminophen, lithium, diazepam, nortryptyline, secobarbital, phenobarbitol.

16. The method of claim 12, wherein said hormones are selected from the group consisting of testosterone, estradiol, 17-hydroxyprogesterone, progesterone, thyroxine, thyroid stimulating hormone, follicle stimulating hormone, and luteinizing hormone.

17. The method of claim 1, wherein said method further comprises contacting said oral fluid sample with a chelator of divalent cations and said oral fluid sample is assayed in a lateral flow immunochromatography assay.

18. The method of claim 17, wherein said bile salt or bile acid is deoxycholic acid or deoxycholate salt;

said chelator is EDTA.

* * * * *

UNITED STATES PATENT AND TRADEMARK OFFICE
CERTIFICATE OF CORRECTION

PATENT NO. : 5,871,905

DATED : February 16, 1999

INVENTOR(S) : Thieme *et al.*

It is certified that error appears in the above-identified patent and that said Letters Patent is hereby corrected as shown below:

Claim 1, col. 23, line 1, please delete "a bile acid bile or salt" and substitute therefore --a bile acid or bile salt--;

Claim 1, col. 23, line 2, please delete "bile or salt" and substitute therefore --or bile salt--;

Claim 2, col. 23, line 6, please delete "bile acid bile or" and substitute therefore --bile acid or bile--;

Claim 13, col. 24, line 9, please delete "*pylon*" and substitute therefore --*pylori*--.

Signed and Sealed this

Fourth Day of April, 2000

Q. TODD DICKINSON

*Attest:*

*Attesting Officer*     *Director of Patents and Trademarks*